(12) United States Patent
Bille

(10) Patent No.: US 7,510,283 B2
(45) Date of Patent: Mar. 31, 2009

(54) HIGH RESOLUTION IMAGING FOR DIAGNOSTIC EVALUATION OF THE FUNDUS OF THE HUMAN EYE

(75) Inventor: Josef F. Bille, Heidelberg (DE)

(73) Assignee: Heidelberg Engineering Optische Messsysteme GmbH, Heidelberg (DE)

( * ) Notice: Subject to any disclaimer, the term of this patent is extended or adjusted under 35 U.S.C. 154(b) by 728 days.

(21) Appl. No.: 10/718,406

(22) Filed: Nov. 20, 2003

(65) Prior Publication Data
US 2005/0110948 A1  May 26, 2005

(51) Int. Cl.
A61B 3/02 (2006.01)
A61B 3/10 (2006.01)
A61B 3/14 (2006.01)
(52) U.S. Cl. .......... 351/243; 351/211; 351/221
(58) Field of Classification Search ......... 351/206, 351/208, 209, 211, 216, 221, 220, 233, 237, 351/243
See application file for complete search history.

(56) References Cited

U.S. PATENT DOCUMENTS 5,943,133 A * 8/1999 Zeylikovich et al. ....... 356/496
6,210,401 B1 * 4/2001 Lai ............................ 606/12
6,347,244 B1 * 2/2002 Dubnack ................... 600/476
2004/0002694 A1 * 1/2004 Pawlowski et al. ........... 606/4

* cited by examiner

Primary Examiner—Ricky L Mack
Assistant Examiner—Brandi Thomas
(74) Attorney, Agent, or Firm—Nydegger & Associates

(57) ABSTRACT

A system for diagnostically evaluating the health of tissue within the fundus of an eye includes a fs laser source, an adaptive optical assembly, an imaging unit, and a computer. The adaptive optical assembly focuses a laser beam to a focal point in the fundus of the eye, and scans the fundus tissue according to a predetermined scanning pattern. Illumination of anisotropic tissue within the fundus, such as the photoreceptors and the Henle-fiber layer, induces a Second Harmonic Generation (SHG) response. Red photons, with a wavelength ($\lambda$) of about 880 nm, are converted to blue photons, with a wavelength of $\lambda/2$, through the process of photon conversion. An imaging unit senses the blue photon return light, and uses the return light to generate an image of the fundus. The computer processes the image, and compares it to a template of healthy tissue to evaluate the health of the imaged tissue.

32 Claims, 3 Drawing Sheets

HIGH RESOLUTION IMAGING FOR DIAGNOSTIC EVALUATION OF THE FUNDUS OF THE HUMAN EYE

FIELD OF THE INVENTION

The present invention pertains generally to ophthalmic diagnostic equipment. More particularly the present invention pertains to a system and apparatus for evaluating the health of tissue within the fundus of an eye. The present invention is particularly, but not exclusively, useful as a system and apparatus for Second Harmonic Generation (SHG) imaging of the tissue in the fundus of a human eye to determine whether the tissue is healthy or damaged.

BACKGROUND OF THE INVENTION

The development of ultra-fast, ultra-short pulsed lasers as surgical tools for ophthalmic surgery has led to a need for enhanced diagnostic capabilities. For example, recent advances in optical surgery techniques include the use of femto-second (fs) lasers for intrastromal and non-invasive refractive surgery. For many of these techniques, high resolution optical imaging is required to thoroughly evaluate the precision, efficiency and effectiveness of these fs surgical lasers. In addition to its use with surgical procedures, it is known that high resolution optical imaging may also be used as a diagnostic tool. In particular, high resolution optical imagining may be useful in some instances to evaluate the health of various parts of the eye, such as the fundus. For instance, it is known that by imaging and studying layers of the fundus, it is possible to detect the early onset of many optical maladies such as age related macular degeneration and glaucomateous disease.

The anatomy of the fundus of an eye is known to comprise several distinct layers, to include axons, ganglion cells, bipolar cells, photoreceptors (rods and cones), pigment cells and the choroid. Further, it is well known that healthy photoreceptors within the fundus of the eye are all aligned substantially parallel to each other. Also, healthy photoreceptors are separated from each other through a distance of about two microns by regions of matrix material. On the other hand, misshapen and misaligned receptors, that are not substantially parallel to each other, are indicative of an unhealthy fundus and, thus, a potential problem. In addition to the photoreceptors, the health of other layers of the fundus can be evaluated. For example, the Henle-fibers are the axons of the bi-polar cells, connecting the photoreceptor signal to the brain. In a healthy Henle-fiber layer, the Henle-fibers have a very specific directional orientation. On the other hand, distortions in the Henle-fiber layer and the orientations of the fibers may be an early indication of age related macular degeneration.

It is important to note that much of the tissue in the fundus of an eye is substantially asymmetrical or anisotropic in nature. Of particular interest here is that the transverse structural properties of the fundus tissue are different from its longitudinal structural properties. In large part this difference is due to the presence of collagen and nerve fibers in the fundus tissue. Importantly, the asymmetrical, anisotropic nature of the fundus tissue offers the possibility that the fundus can effectively respond to Second Harmonic Generation ("SHG") imaging.

As a general proposition, SHG imaging is due to the second order, non-linear, polarization of light as it is radiated from an illuminated sample. For instance, during SHG it happens that red photons are converted into blue photons by a phenomenon which is commonly referred to as "photon conversion". Specifically, it happens that two incident red photons (with wavelengths $\lambda$ on the order of 880 nm) are converted to a single, radiated blue photon (with a wavelength of $\lambda/2$ or 440 nm). The SHG response or return light that is so generated, with a wavelength of 440 nm, can be used to create an image of the illuminated tissue.

Importantly, the SHG response induced by the illumination of anisotropic tissue in the fundus is non-linear. Due to this non-linearity, the SHG response will increase with the square of the power density of the incident laser beam. It should be noted here that the power density of the incident laser beam is a function of both the input energy and the volume of the focal point. It follows, therefore, that the power density of the incident laser beam can be increased if the illuminated volume, or more specifically the Point Spread Function ("PSF") of the laser beam focal point, can be reduced. In this context, the PSF is a three dimensional volumetric measurement that defines the finest volume of focus for a particular light beam. For many presently used laser systems, the PSF is generally on the order of 6 μm×6 μm×200 μm. With adaptive optics, however, it is possible to reduce the PSF to about 2 μm×2 μm×20 μm. This represents a reduction in volume by a factor of about 100. Accordingly, when the PSF is reduced by a factor of about 100, there is a corresponding increase in the power density, also by a factor of about 100. Adaptive optics, such as those disclosed in U.S. Pat. No. 6,220,707, entitled "Method for Programming an Active Mirror to Mimic a Wavefront" issued to J. Bille, offer the potential to effectively focus the incident beam to a smaller PSF, while maintaining a substantially aberration-free beam of light.

Due to its anisotropic nature, the fundus of the eye is well suited for SHG imaging. Specifically, various layers of the fundus tissue, to include the photoreceptors, the nerve fiber layer and the Henle-fibers, contain anisotropic tissue. Further, the anisotropic tissues are surrounded by a substantially isotropic matrix. Consequently, the anisotropic tissues will produce a SHG response when illuminated, while the surrounding isotropic materials will produce no such response. An important additional consideration is that the geometry of the various fundus layers is compatible with the smaller PSF desired for SHG imaging. Specifically, the distance between anisotropic elements in the various layers of the fundus, such as the distance between healthy photoreceptors, is on the order of 2 μm. Also, the depth of the various layers is generally equal to or greater than 20 μm. It is therefore possible, with a PSF of 2 μm×2 μm×20 μm, to detect a single element, such as a photoreceptor, within a single layer of the fundus, and to determine its location in the fundus relative to other elements.

In light of the above, it is an object of the present invention to provide a system for imaging the fundus of the human eye. Another object of the present invention is to provide a system which can resolve the various individual tissue layers of the fundus, particularly the photoreceptor layer, for diagnostically evaluating the health of the various fundus tissues. Still another object of the present invention is to provide a system for imaging the fundus of the human eye that produces a Second Harmonic Generation image. Yet another object of the present invention is to provide a system for imaging the fundus of the human eye that is easy to use, relatively simple to manufacture and comparatively cost effective.

SUMMARY OF THE INVENTION

The present invention pertains to a diagnostic system and method for determining the health of tissue in the fundus of an eye. Included in the system of the present invention is a laser source for generating a laser beam, an optical assembly for directing and focusing the laser beam onto the fundus, and a computer for evaluating the return light that results when the laser beam is incident on the fundus of the eye. The system may also include adaptive optics for more precisely focusing the laser beam, and a wavefront sensor for detecting the alignment of the eye prior to imaging. Based on the resultant computer evaluation, the basic health of the fundus is determined.

For the present invention, the laser source is capable of generating a beam of pulses with each pulse having a duration of about 200 femtoseconds. Further, the wavelength of light in the laser beam will be in a range between 700 nm and 100 nm and, preferably, will have a wavelength of about 880 nm. The pulse energy level will be around 1 nJ.

When focused on the fundus, a focal point of the laser beam may generally be on the order of 6 µm×6 µm×200 µm, which is adequate for imaging much of the fundus layer. It is an important aspect of the present invention, however, that the adaptive optics are able to focus the pulses in the laser beam to spot size having about a 2 micron diameter. More specifically, it is envisioned that the pulses of the laser beam be focused to a spot size that has a PSF of approximately 2 µm×2 µm×20 µm. A smaller PSF provides for finer resolution of fundus tissue, such as the photoreceptors in the foveola.

In the operation of the system of the present invention, the laser beam is initially focused onto the fundus of the eye at a start point, and is then moved through a scanning sequence. In this scanning sequence, the laser beam is moved to a succession of focal points along a predetermined path over the fundus. Importantly, each of the laser beam's focal points is adjacent to at least one other focal point so that all of the focal points are effectively contiguous. Depending on the area of the fundus that is to be diagnosed, the path of focal points can be such that it effectively covers the desired area.

At each focal point in a scanning sequence, the laser source is activated to radiate fundus tissue at the focal point with approximately five laser pulses. After irradiation, the tissue will then respond in one of several ways. For one, the laser light may be absorbed by the tissue and, thereby, cause no return light. As another response, it may happen that the 880 nm wavelength light of the laser beam is reflected by the fundus tissue. For still another response, due to the anisotropic nature of the tissue (e.g. a photoreceptor), the incident light may experience the "photon conversion" phenomenon. In this case, the tissue will generate return light having a wavelength of 440 nm. In each instance, the separate responses from each focal point are identified by the computer and collectively evaluated.

During the evaluation of a scanning sequence, the computer uses the various responses to determine the relative locations of photoreceptors (i.e. anisotropic tissue) in the fundus. Thus, an image pattern of the fundus can be generated and compared with a template pattern which would indicate normal healthy tissue in the fundus.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
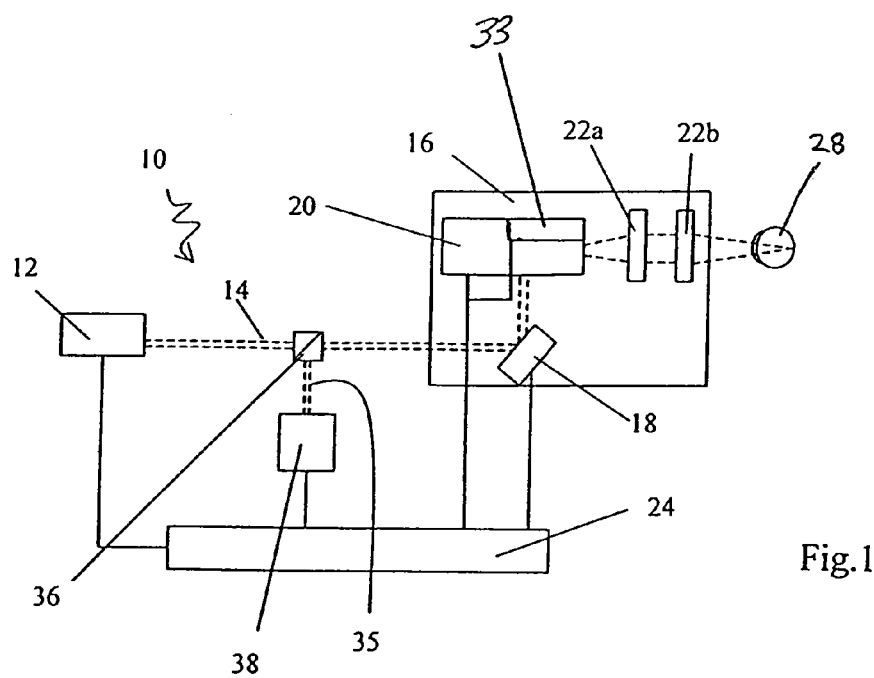
FIG. 1 is a schematic of the system of the present invention showing the interrelationship of the components.

A system in accordance with the present invention is shown in FIG. 1 and generally designated 10. As shown in FIG. 1, the system 10 includes a laser source 12 for generating a laser beam 14. As contemplated by the present invention, the laser source 12 is a femtosecond (fs) laser source 12, capable of generating a laser beam 14 with a pulse repetition rate of 100 million pulses/second. Importantly, the wavelength of an individual pulse of the laser beam 14 is in the range between 700 nm to 1000 nm. In the preferred embodiment of the present invention, the laser source 12 is a tunable laser source 12, and the preferred wavelength of the laser beam 14 is 880 nm. The laser beam 14 has an energy level of 1 nJ/pulse, with a pulse duration of 100 fs.

As shown in FIG. 1, the system 10 includes an optical assembly 16 for directing and focusing the laser beam 14. In the preferred embodiment of the present invention, the optical assembly 16 includes adaptive optics which comprise an active mirror 18, a scanning unit 20 and at least two focusing lenses, of which lenses 22a and 22b are exemplary. It is envisioned for the present invention that the active mirror 18 is of the type disclosed in U.S. Pat. No. 6,220,707, entitled "Method for Programming an Active Mirror to Mimic a Wavefront" issued to J. Bille. The active mirror 18 is in electronic communication with a computer 24, as are the laser source 12 and the scanning unit 20.

An important aspect of the present invention is that the computer 24 programs the active mirror 18 to "compensate" the laser beam 14 as it reflects off the surface of the active mirror 18. In order to better understand the need for laser beam 14 compensation, it is necessary to refer momentarily to FIG. 2. It can be seen by referring to FIG. 2 that the aperture diameter 26 of the eye 28, created by the iris 30, should be extended during the operation of the present invention. It is well known that when the aperture diameter 26 is extended, the concavity and irregularities of the cornea 32 will tend to distort a beam of light entering the eye 28. These distortions will tend to defocus the beam of light as it transits the cornea 32. It happens that in order to image a larger percentage of the fundus region, to include the peripheral regions of the photoreceptor layer, a focal point 34, which is actually defined by a volume, may be on the order of 6 µm×6 µm×200 µm. In the preferred embodiment of the present invention, however, the laser beam 14 must be more precisely focused. The focal point 34 may be as small as 2 µm×2 µm×20 µm. This volume is a Point Spread Function (PSF), and it is by definition the finest volume of focus for the laser beam 14. In order to achieve a PSF of 2 µm×2 µm×20 µm, the aperture diameter 26 of the eye 28 must be on the order of six millimeters (6 mm). An aperture diameter 26 of 6 mm, however, will lead to laser beam 14 distortion. It is necessary, therefore, to compensate the laser beam 14 with the active mirror 18 to reduce or eliminate beam distortions, and thereby achieve the desired PSF.

In order to compensate the active mirror 18 to achieve a PSF of 2 µm×2 µm×20 µm, the computer 24 must know the precise alignment of the eye 28. Alignment data may be received by the computer 24 from a source other than the optical assembly 16, or the optical assembly 16 may include a wavefront sensor 33. In the preferred embodiment of the present invention, the optical assembly 16 includes a wavefront sensor 33 in electronic communication with the computer 24.

Still referring to FIG. 1, the scanning unit 20 of the optical assembly 16 may be of any type well known in the pertinent art that is capable of focusing the laser beam 14 along a pre-determined beam path. The movement of the scanning unit 20 during imaging is controlled by the computer 24, in accordance with a predetermined scanning sequence. As can be seen in FIG. 1, the scanning unit 20 is optically aligned with focusing lenses 22a and 22b. After transiting the focusing lenses 22a and 22b, the beam 14 is focused on the desired focal point 34 in the eye 28 of the patient.

In addition to directing and focusing the laser beam 14 in transmission, the adaptive optical assembly 16 receives and redirects a response signal consisting of a return light 35 as well. Specifically, the active mirror 18 is optically aligned with a beam splitter 36 for directing the return light 35 toward the beam splitter 36. The beam splitter 36, in turn, is optically aligned with an imaging unit 38 for directing the return light 35 into the imaging unit 38. As shown in FIG. 1, the imaging unit 38 is in electronic communication with the computer 24. Once the return light 35 is received and processed by the imaging unit 38, the image data is transmitted to the computer 24 for further processing and analysis.

Figure 2:
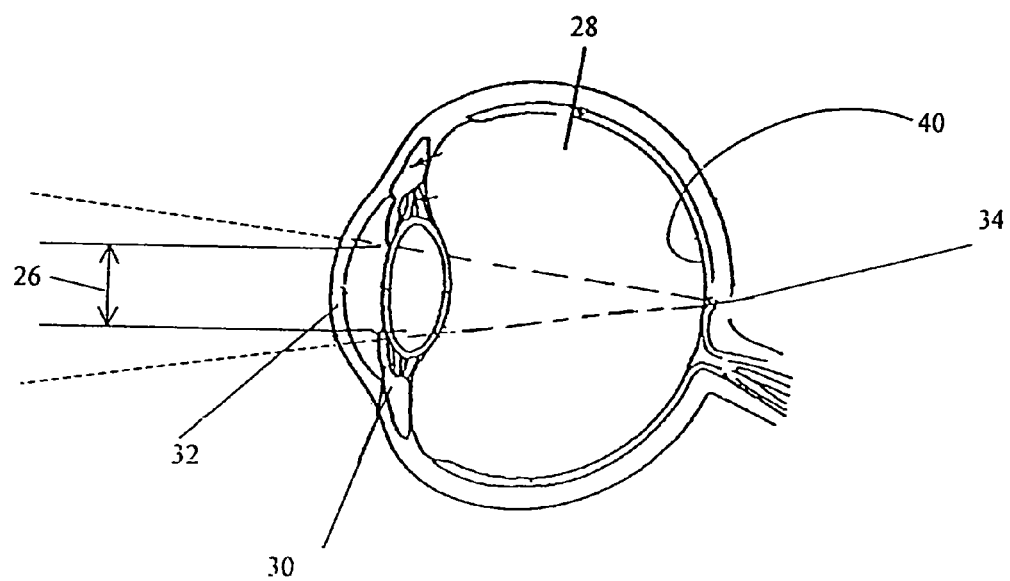
FIG. 2 is an anatomical cross section of a human eye wherein the fundus is illuminated by a laser beam.

In operation, the laser source 12 generates a laser beam 14 which is directed toward the adaptive optical assembly 16, more specifically toward the active mirror 18. As the laser beam 14 reaches the active mirror 18, the active mirror 18 redirects the laser beam 14 into the scanning unit 20. After receiving the laser beam 14, the scanning unit 20 directs the beam 14 through the focusing lenses 22a and 22b, to focus the laser beam 14 on a focal point 34 in the fundus 40 of the eye 28 (FIG. 2).

As the scanning unit 20 continues to direct the laser beam 14 into the fundus 40 of the eye 28, the scanning unit 20 periodically moves the laser beam 14 from one focal point 34 to an adjacent focal point 34. The movement of the focal point 34 is in accordance with the predetermined scanning sequence. Each focal point 34 is illuminated with about five pulses. The consequence of moving the laser beam 14 from one focal point 34 to an adjacent focal point 34, according to a predetermined scanning sequence, is that the focal points 34 for the present invention are essentially contiguous.

As the scanning unit 20 continues to scan, the laser beam 14 illuminates either structurally anisotropic tissue (collagen, nerve fibers, etc.) or isotropic matrix material within the fundus 40. As the laser beam 14 illuminates and interacts with the fundus 40 tissues, one of several responses may occur. When the laser beam 14 illuminates anisotropic tissue, a response signal consisting of a return light 35 will be generated, as discussed in greater detail below. A second possible response, however, is that the incident laser beam 14 is reflected at a wavelength of about 880 nm. Yet a third possibility is that isotropic regions of the fundus 40 are illuminated. When the isotropic regions of the fundus 40 are illuminated, the incident laser beam 14 is absorbed, and no response is produced. All three possible "responses" are used by the system 10 to generate a diagnostic image of the fundus 40.

Figure 3:
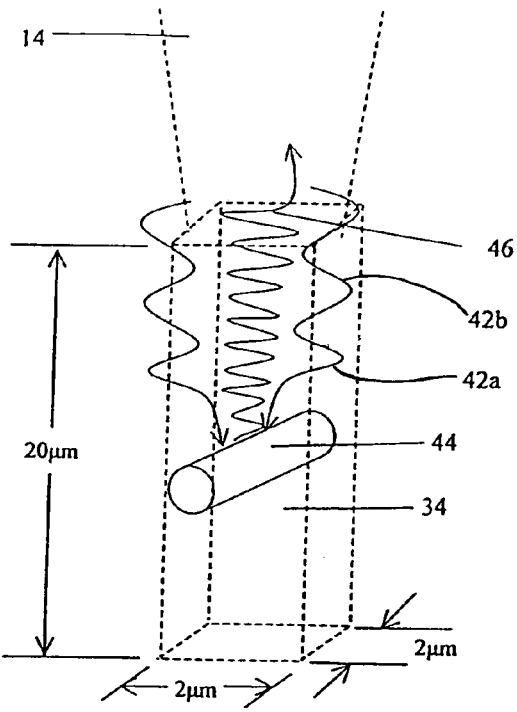
FIG. 3 is a representative illustration of a focal point in the fundus of the eye.

Referring now to FIG. 3, the interaction of the laser beam 14 and the anisotropic fundus 40 tissue is shown in greater detail. The laser beam 14 is depicted as a train of red photons, of which the photons 42a and 42b are exemplary. In the preferred embodiment of the present invention, the wavelength of the red photons 42a and 42b is about 880 nm. In transmission, the photons 42a and 42b illuminate the focal point 34, which has a PSF of 2 µm×2 µm×20 µm. If the red photons 42a and 42b strike collagen tissue 44, or other anisotropic tissues within the fundus 40, a Second Harmonic Generation (SHG) response is produced. More specifically, a SHG response is produced when the two red photons 42a and 42b are converted into a single blue photon 46 through a phenomenon known as "photon conversion". Importantly, the success of the photon conversion and the intensity of the SHG response are dependent upon the power density of the incident laser beam 14. Power density, in turn, is a function of the input energy and the size of the PSF. It follows, therefore, that when a PSF on the order of 2 µm×2 µm ×20 µm is illuminated by an ultra-fast, ultra-short pulsed fs laser beam 14, a SHG response consisting of a return light 35 will be produced.

The SHG return light 35 travels on a return path through the scanning unit 20, and is reflected by the active mirror 18 into the beam splitter 36. The beam splitter 36 directs the return light 35 to the imaging unit 38. The imaging unit 38 collects and collates the return light 35, it records the non-responses, and it generates a corresponding response pattern. The response pattern is then used by the imaging unit 38 to create an image of the fundus 40 region. The image produced is transmitted to the computer 24 for further processing. In the computer 24, the image is compared to a template for healthy fundus 40 tissues. By comparing the image generated by the return light 35 with a template for healthy tissue, the computer 24 can diagnostically evaluate the health of the imaged tissue.

Figure 4:
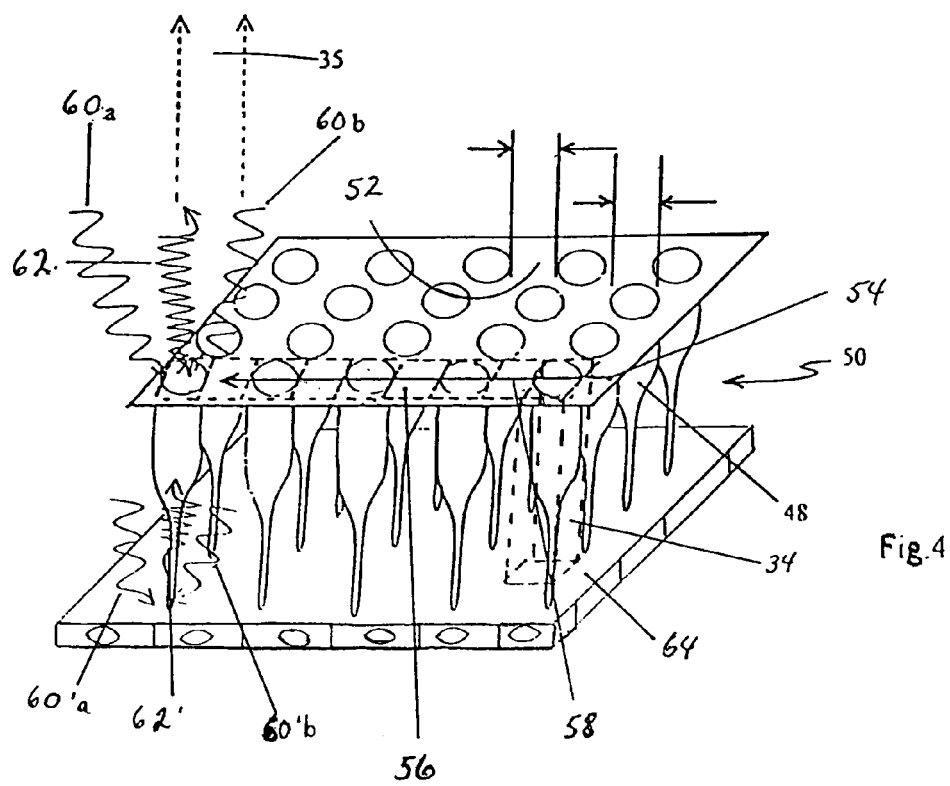
FIG. 4. is a representative illustration of an illuminated photoreceptor within the fundus of the eye.

In one application of the present invention, the system 10 is used to image the photoreceptors 48 in the photoreceptor layer 50 of the fundus 40 of the eye 28. Importantly, as shown in FIG. 4, healthy photoreceptors 48 are substantially parallel to each other, and they are uniformly spaced within the photoreceptor layer 50. Unhealthy photoreceptors 48 are generally misaligned or otherwise spatially distorted.

Still referring to FIG. 4, it can be seen that the width of the photoreceptor 48 is about 2 µm. In addition, the width of the gap 52 between each photoreceptor 48 may be as much as 2-4 µm. As such, it is possible for the laser beam 14 to illuminate a single photoreceptor 48, or a single gap 52, with a focal point 34 which is approximately 2 µm wide.

As shown in FIG. 4, the laser beam 14 is initially focused on a start point 54. The laser beam 14 scans the photoreceptor layer 50 according to a predetermined scanning sequence, of which sequence 56 and arrow 58 in FIG. 4 are exemplary. As the laser beam 14 scans, the focal point 34 will alternately focus on a photoreceptor 48 or a gap 52. When the laser beam 14 illuminates a photoreceptor 48, the anisotropic nature of the photoreceptor 48 tissue (e.g. collagen 44) induces photon conversion and a blue photon return light 35. More specifically, as red photons 60a-b and 60'a-b illuminate the photoreceptor 48, the red photons 60a-b and 60'a-b are converted to blue photons 62 and 62'. An important aspect of the present invention is that the SHG return light 35 actually consists of a backscattered component or first blue photon 62, and a forward scattering component or second blue photon 62'. The second blue photon 62' is reflected by the pigment layer 64. Despite the relatively low reflective value (approximately 3%) of the pigment layer 64, the reflected photon 62' may be stronger than the backscattered photon 62. The sum of the backscattered photon 62, and the forward scattered photon 62', is the SHG response consisting of return light 35. When the isotropic material in the gaps 52 of the photoreceptor layer 50 is illuminated, photon conversion does not occur. Consequently, a SHG return light 35 is not generated. The scanning sequence 56, therefore, produces an image that distinguishes the photoreceptors 48 from the surrounding matrix material. For a healthy photoreceptor layer 50, the image will be one of parallel receptors 48 surrounded by uniformly dispersed matrix material.

In addition to using the SHG return light 35 to create an image of the fundus 40 tissue, the intensity of the return light 35 can be used to assess the alignment of the photoreceptors 48. Photoreceptors 48 that are vertical with respect to the pigment layer 64 will generate the most intense SHG return light 35. The more "tilted" the photoreceptor 48, the less intense the return light 35. By comparing return light 35 intensities with predetermined threshold values for light intensity, the system 10 can evaluate the alignment, and hence the health, of the photoreceptors 48.

Figure 5:
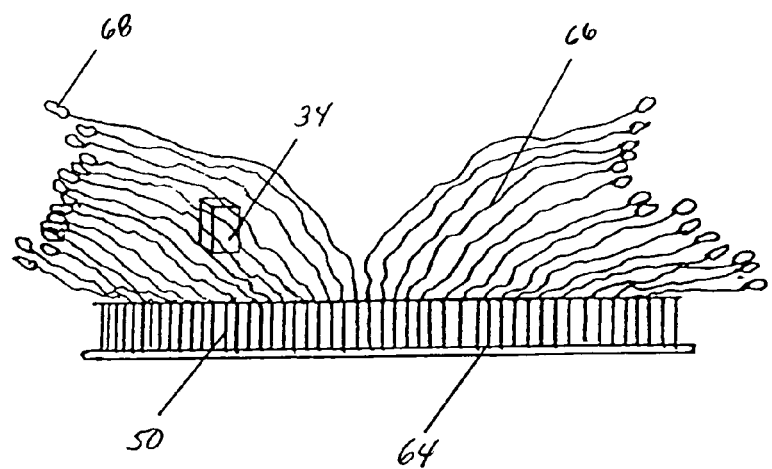
FIG. 5 is an anatomical cross-section of a portion of the eye showing the fovea connected to the optical nerve.

In another application of the present invention, the Henle-fibers 66, which are the axons of the bipolar cells 68, can be imaged and diagnostically evaluated. The Henle-fibers 66 connect the photoreceptor signal to the brain, and a distortion of the directional structure of the fibers 66 can be an early indication of age related macular degeneration. As shown in FIG. 5, a three-dimensional focal point 34 on the order of 2 µm×2 µm×20 µm provides for imaging of the individual fibers 66 within the Henle-fiber layer.

Figure 6A:
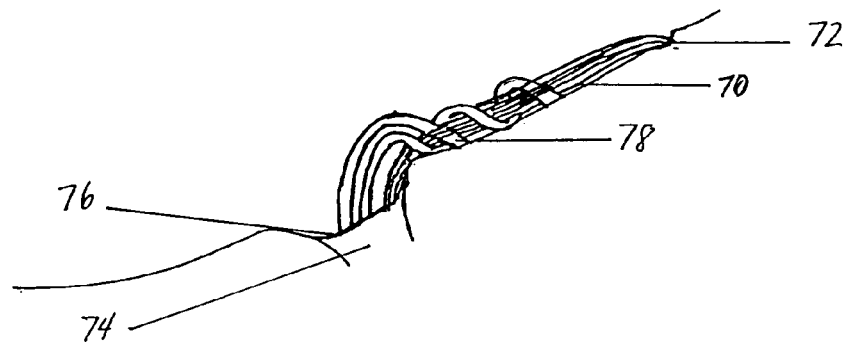
FIGS. 6A and 6B are representative top-views of the fovea, the nerve fiber bundles, and the optical disk.
Figure 6B:
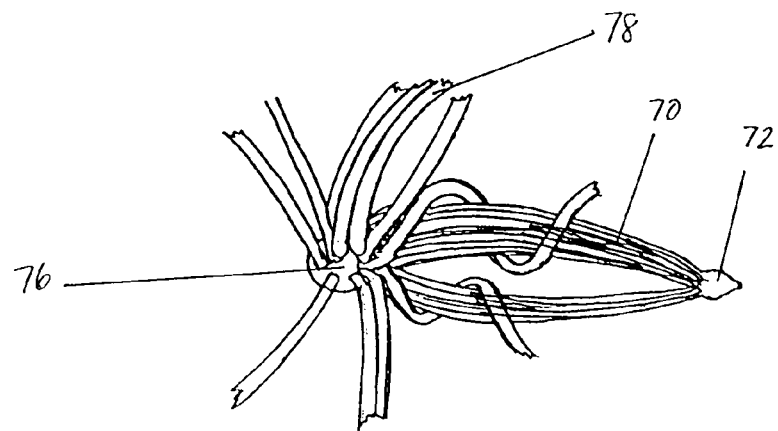

In yet another application of the present invention, the nerve fiber layer of the eye 28 can be imaged to detect the onset of glaucoma. In FIGS. 6A and 6B, the thin nerve fibers 70 of the papillomacular fiber bundle connect the fovea 72 to the optic nerve 74, passing through the optical disk 76 at the edges of the disk 76. Bundles of larger nerve fibers 78, coming from the so-called peripapillary or periphery area of the eye 28, cross through and over the papillomacular bundle, and slope through the center section of the optical disk 76. As a result of the larger nerve fibers 78 overlapping the thinner nerve fibers 70, the thinner fibers 70 are buried deep within the nerve fiber layer. Not surprisingly, the thinner nerve fibers 70 are very difficult to diagnose. It is well known that pressure on the eye 28 may damage the nerve fibers 70 and 78, leading to glaucoma. Visual field loss which can be perceived by the patient occurs if at least 20% of the nerve fibers 70 and 78 are damaged or destroyed. There are approximately 1.4 million nerve fibers, therefore, damage to more than about 300,000 fibers will produce a noticeable loss of vision. This loss of vision is first perceived by the patient in the peripheral vision. However, under pressure, the thinner fibers 70 will tend to break first. Identifying damage to the thinner fibers 70 of the nerve fiber layer, well before the thicker fibers 78 are damaged, can provide an early warning of glaucoma. SHG imaging provides an opportunity to image these thin fibers 70, as well as the larger fibers 78, for diagnostic evaluation. In addition to imaging the fibers 70 and 78 to detect damage, SHG imaging can be used to count the number of healthy fibers 70 and 78. The progression of glaucoma can be monitored and evaluated by periodic counting of the number of healthy fibers, and comparing the number of healthy fibers remaining to previous evaluations.

While the particular High Resolution Imaging for Diagnostic Evaluation of the Fundus of the Human Eye as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for diagnostically evaluating the health of tissue within the fundus of an eye, which comprises:
    a laser source for generating a laser beam, said laser beam having a plurality of laser pulses, wherein each laser pulse has a first wavelength and a pulse duration less than approximately two hundred femtoseconds;
    an optical assembly for focusing each laser pulse to a focal point in the fundus, with the focal point being characterized by a spot size having a diameter of approximately two microns, wherein the laser pulses of the first wavelength illuminate tissue to induce a second harmonic generation (SHG) response of a second wavelength, by photon conversion, when the laser beam is incident on anisotropic tissue in the fundus, with said SHG response of the second wavelength being used to create an image;
    a means for detecting the SHG response; and
    a computer for evaluating the image of the SHG response in comparison with a template for healthy tissue to determine the health of the fundus tissue.

2. A system as recited in claim 1 wherein said first wavelength is in the range between 700 nm to 1000 nm, and further wherein said second wavelength is in the range between 350 nm to 500 nm.

3. A system as recited in claim 2 wherein said first wavelength is 880 nm.

4. A system as recited in claim 1 wherein a pulse of said laser beam has an energy level of 1 nJ.

5. A system as recited in claim 1 wherein said optical assembly includes adaptive optics.

6. A system as recited in claim 5 wherein said optical assembly further comprises:
    an active mirror;
    a scanning unit for periodically moving said laser beam from one focal point to an adjacent focal point in the fundus, to focus said laser beam on a plurality of focal points within said fundus;
    two focusing lenses;
    a wavefront sensor for generating data indicative of an alignment of the eye; and
    a computer for receiving the data from said wavefront sensor for use in controlling said active mirror to direct said laser beam to the focal point.

7. A system as recited in claim 1 wherein said laser beam irradiates a focal point with about five laser pulses.

8. A system as recited in claim 1 wherein said detecting means comprises an imaging unit in electronic communication with a computer.

9. A system as recited in claim 1 wherein said evaluating means uses a pattern of the SHG response to evaluate the health of the fundus tissue.

10. A system as recited in claim 1 wherein said evaluating means compares an intensity level of said SHG response to a predetermined threshold value of light intensity to evaluate the health of the fundus tissue.

11. A system as recited in claim 1 wherein the SHG response includes a plurality of responses, and further wherein said evaluating means counts the number of SHG responses to evaluate the health of the fundus tissue.

12. A method for diagnostically evaluating the health of tissue within the fundus of an eye which comprises the steps of:
    dilating the iris of the human eye to create an aperture having an extended diameter;

directing a laser beam generated by a laser source through said aperture to a focal point in said fundus of said eye, said laser beam having a plurality of laser pulses, wherein each laser pulse has a first wavelength and a pulse duration less than approximately two hundred femtoseconds;

scanning said focal point between anisotropic tissue and isotropic tissue in said fundus;

inducing photon conversion with the laser pulses of the first wavelength generated by the laser source, when said focal point is directed at anisotropic tissue to generate a return light from the tissue, wherein the return light is a second harmonic generation (SHG) response having a second wavelength;

absorbing the laser beam when said focal point is directed at isotropic tissue;

detecting the return light having a second wavelength generated by anisotropic tissue to create an image;

detecting the absorption of the laser beam by isotropic tissue; and evaluating the image created by the return light in comparison with a template to determine the health of the fundus tissue.

13. A method as recited in claim 12 wherein said extended diameter is approximately six millimeters (6 mm).

14. A method as recited in claim 12 wherein the energy level of said laser pulse is 1 nJ.

15. A method as recited in claim 12 wherein said first wavelength is in the range between 700 nm to 1000 nm, and further wherein said second wavelength is in the range between 350 nm to 500 nm.

16. A method as recited in claim 15 wherein said first wavelength is 880 nm.

17. A method as recited in claim 12 wherein said directing step further comprises the steps of:

programming an active mirror to compensate said laser beam;

reflecting said laser beam off said active mirror to direct said laser beam through a scanning unit and at least two focusing lenses; and periodically moving said laser beam from one focal point to an adjacent focal point in the fundus during the scanning step, to focus said laser beam on a plurality of focal points within said fundus.

18. A method as recited in claim 17 which further comprises the step of receiving data indicative of an alignment of the eye from a wavefront sensor for programming said active mirror to direct said laser beam to the focal point.

19. A method as recited in claim 12 wherein said laser beam irradiates a focal point with about five laser pulses.

20. A method as recited in claim 12 wherein said evaluating step further comprises the steps of:

identifying a pattern of said return light; and evaluating said pattern to determine the health of the fundus tissue.

21. A method as recited in claim 12 wherein said evaluating step further comprises the steps of:

quantifying the intensity level of said return light; and comparing said intensity level to predetermined threshold levels of light intensity for determining the health of the fundus tissue.

22. A method as recited in claim 12 wherein said return light includes a plurality of responses, and further wherein said evaluating step further comprises the step of counting the number of return light responses for evaluating the health of the fundus tissue.

23. An apparatus for diagnostically evaluating the health of tissue within the fundus of an eye, which comprises:

a laser source for generating a laser beam, said laser beam having a plurality of laser pulses, wherein each laser pulse has a first wavelength and a pulse duration less than approximately two hundred femtoseconds;

an optical assembly for focusing each laser pulse to a focal point in the fundus, said focal point being characterized by a spot size having a diameter of approximately two microns, wherein the laser pulses of the first wavelength illuminate tissue to induce a second harmonic generation (SHG) response of a second wavelength, by photon conversion, when the laser beam is incident on anisotropic tissue in the fundus, with said SHG response having a second wavelength;

an imaging unit for detecting the SHO response as an image; and a computer for evaluating the image created by said SHG response in comparison with a template to determine the health of said fundus tissue.

24. An apparatus as recited in claim 23 wherein said first wavelength is in the range between 700 nm to 1000 nm, and further wherein said second wavelength is in the range between 350 nm to 500 nm.

25. An apparatus as recited in claim 23 wherein said first wavelength is 880 nm.

26. An apparatus as recited in claim 23 wherein said optical assembly includes adaptive optics.

27. An apparatus as recited in claim 26 wherein said optical assembly further comprises:

an active mirror;

a scanning unit for periodically moving said laser beam from one focal point to an adjacent focal point in the fundus, to focus said laser beam on a plurality of focal points within said fundus;

two focusing lenses; and a wavefront sensor for generating data indicative of an alignment of the eye for use in controlling said active mirror to direct said laser beam to the focal point.

28. An apparatus as recited in claim 23 wherein said laser beam irradiates a focal point with about five laser pulses.

29. An apparatus as recited in claim 23 wherein a pulse of said laser beam has an energy level of 1 nJ.

30. An apparatus as recited in claim 23 which further comprises a means for evaluating a pattern of said SHG response to evaluate the health of the fundus tissue.

31. An apparatus as recited in claim 23 which further comprises a means for comparing an intensity level of said SHG response to predetermined threshold values of light intensity to evaluate the health of the fundus tissue.

32. An apparatus as recited in claim 23 wherein said SHG response includes a plurality of responses, and further wherein the apparatus includes a means for counting the number of SHG responses to evaluate the health of the fundus tissue.

* * * * *

UNITED STATES PATENT AND TRADEMARK OFFICE
CERTIFICATE OF CORRECTION

PATENT NO. : 7,510,283 B2
APPLICATION NO. : 10/718406
DATED : March 31, 2009
INVENTOR(S) : Josef F. Bille It is certified that error appears in the above-identified patent and that said Letters Patent is hereby corrected as shown below:

Column 10, Line 21
DELETE
"SHO"
INSERT
-- SHG --

Signed and Sealed this

Nineteenth Day of May, 2009

JOHN DOLL
*Acting Director of the United States Patent and Trademark Office*